(12) United States Patent
Mashouf (10) Patent No.: US 10,456,218 B1
(45) Date of Patent: Oct. 29, 2019

(54) CONTOURED-BODY ORTHODONTIC EXPANSION SCREW

(71) Applicant: Cameron Mashouf, San Jose, CA (US)

(72) Inventor: Cameron Mashouf, San Jose, CA (US)

(*) Notice: Subject to any disclaimer, the term of this patent is extended or adjusted under 35 U.S.C. 154(b) by 0 days.

(21) Appl. No.: 16/150,207

(22) Filed: Oct. 2, 2018

(51) Int. Cl.
*A61C 7/10* (2006.01)
(52) U.S. Cl.
CPC .................................... *A61C 7/10* (2013.01)
(58) Field of Classification Search
CPC ........................................................ A61C 7/10
USPC ...................................................... 433/7–20
See application file for complete search history.

(56) References Cited

U.S. PATENT DOCUMENTS

2015/0056566 A1* 2/2015 Moon ..................... A61C 7/10
 433/7
2017/0290643 A1* 10/2017 Giardino ................. A61C 7/10

* cited by examiner

*Primary Examiner* — Yogesh P Patel
(74) *Attorney, Agent, or Firm* — Kilpatrick Townsend & Stockton LLP (57) ABSTRACT

Disclosed is a palatal expander for widening a patient's upper jaw that includes portions that are anatomically contoured to the arched shape of a patient's palate. Specifically, the palatal expander includes expansion screws with movable bodies having anatomically contoured palatal surfaces that do not impinge palate tissue during jaw widening procedures. The expansion screws may further include features that allow for reduced hindrances to speech and eating during jaw widening procedures.

7 Claims, 8 Drawing Sheets

CONTOURED-BODY ORTHODONTIC EXPANSION SCREW

FIELD OF THE INVENTION

The present technology is related to palatal expanders, particularly an expansion screw, and the use and manufacture thereof.

BACKGROUND OF THE INVENTION

Figure 1A:
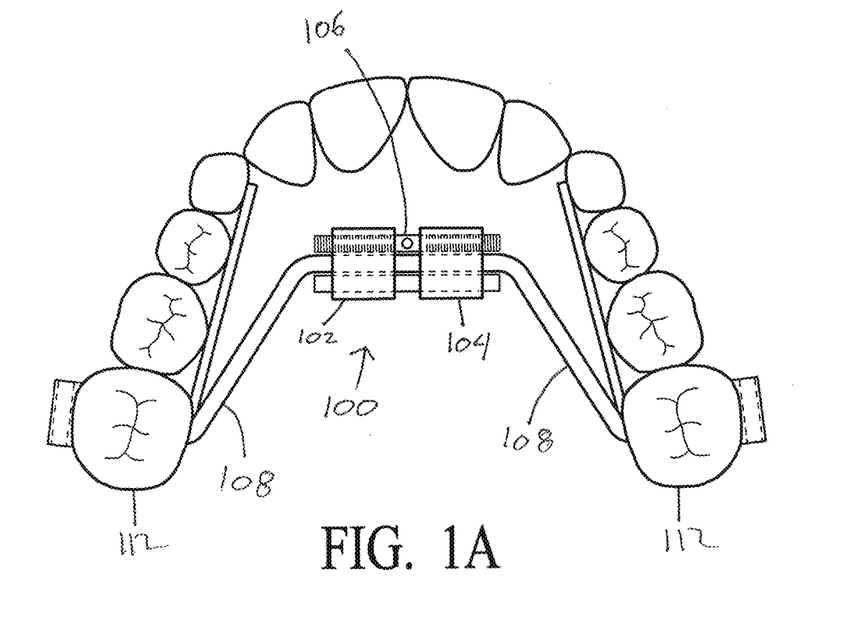
FIG. 1A shows a transverse plane view of an expansion screw in a first un-spread configuration.
Figure 1B:
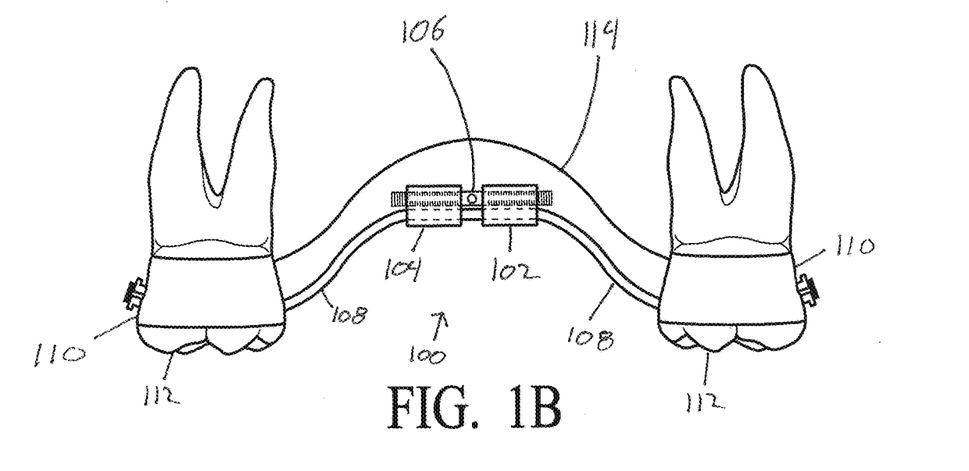
FIG. 1B shows a frontal plane view of the expansion screw of FIG. 1A in the first un-spread configuration.
Figures 1C, 1D:
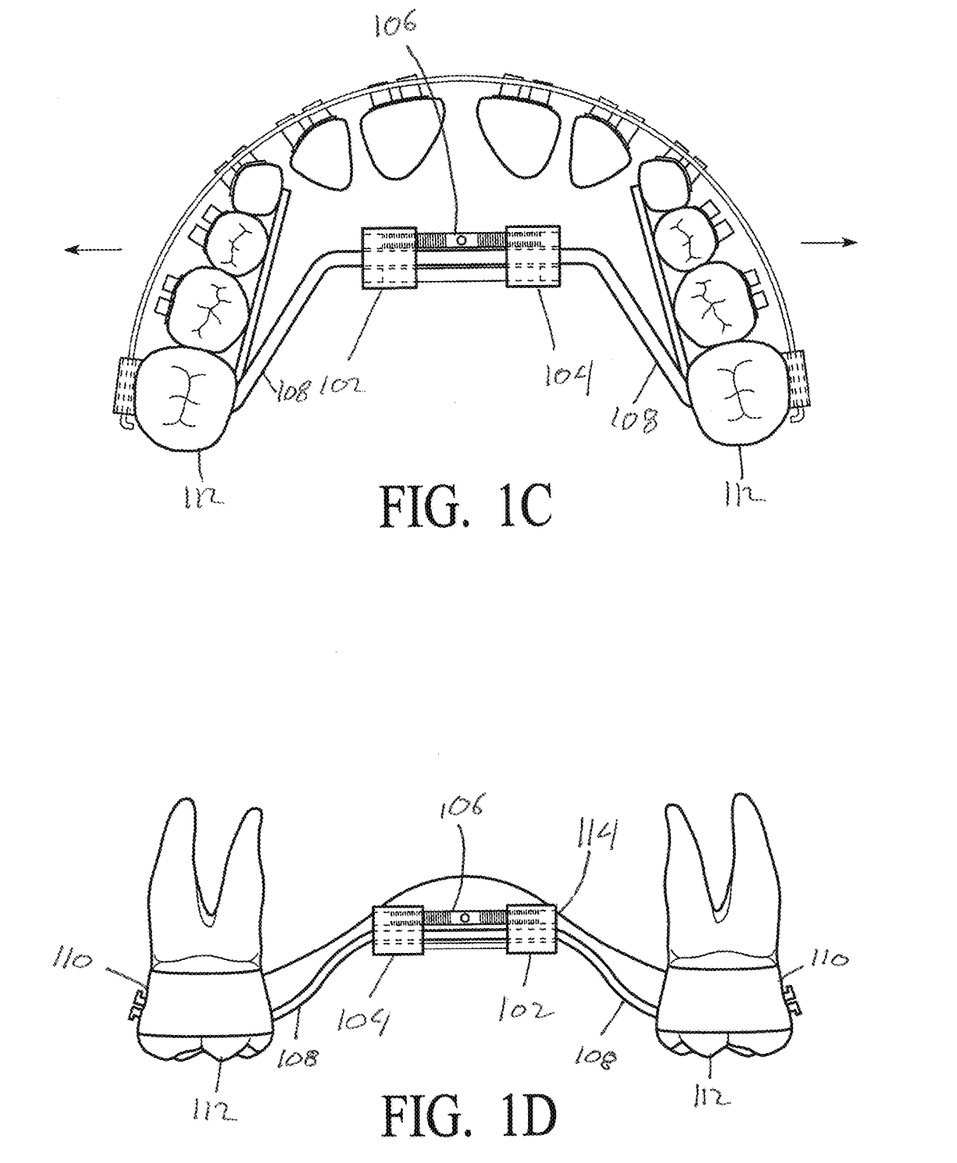
FIG. 1C shows a transverse plane view of the expansion screw of FIG. 1A in a second spread configuration.
FIG. 1D shows a frontal plane view of the expansion screw of FIG. 1A in the second spread configuration.

Orthodontic expansion screws may be used for the generation of an expansion force within the upper jaw of a patient. Expansion screws may be used for separation of the palatal suture for the skeletal widening of the upper jaw. For example, an expansion screw may widen a narrow upper jaw by opening the palatine suture by applying force to straps attached to opposite molars of the upper jaw. As shown in FIGS. 1A-D, an expansion screw 100 may comprise a first body 102 and second body 104. As shown the bodies are rectangular in the frontal plane views of FIGS. 1A and 1C, and rectangular in the transverse plane views if FIGS. 1B and 1D. The first body 102 and the second body 104 are movable via a spindle 106 threadably coupled to the bodies. Supporting wires 108 are coupled to molar bands 110 on opposite sides of the expansion screw 100. FIG. 1A, shows a transverse plane view and FIG. 1B shows a frontal plane view of expansion screw 100 in a first un-spread configuration. By increasing the distance between the first and second bodies pressure between the molar bands attached to maxillary molars 112 is created which is transmitted to the upper jaw. FIG. 1C, shows a transverse plane view and FIG. 1D shows a frontal plane view of expansion screw 100 in a second spread configuration, wherein the distance between the bodies in greater than the distance in the first configuration. Increasing the distance, and therefore the pressure, between the maxillary molars by increasing the distance between the bodies with the spindle will lead to the palatine suture breaking open, widening of the midpalatal suture which will widen the upper jaw. In addition to this mechanism of breaking open and widening the midpalatal suture, expansion screws may further be used to widen an upper jaw via other mechanisms and/or may be used to move a single tooth of group of teeth in either jaw.

As shown in FIGS. 1A-1D, the use of existing expansion screws may lead to portions of the expansion screw impinging palate tissue 114. This impingement may cause discomfort to the patient and it may lead to prolonged treatment due to temporary removal of the expansion screw in order to ease the discomfort. Specifically, as shown in FIG. 1B, in the first configuration the bodies 102 and 104 do not contact the palate tissues 114. With the distance between the bodies increased to the second configuration, as shown for example in FIG. 1D, the top corners of the rectangular bodies 102 and 104 impinge the palate tissue 114. Further, the front left and right corners of the bodies 102 and 104 in a transverse view may further impinge the palate tissue. This impingement is particularly problematic for patients with deep and narrow palates, and for large amounts of expansion between the bodies, for example greater than 10 mm. If discomfort is severe, the expansion screw may be removed temporarily, which may prolong treatment due to the interruption caused by the removal.

Therefore it is desirable for an expansion screw to be able to expand in deep and narrow palates and/or expand greater than 10 mm without impinging corners of the bodies into palate tissue.

BRIEF SUMMARY OF THE INVENTION

The present invention relates to palatal expanders for widening a patient's upper jaw that include portions that are anatomically contoured to the arched shape of a patient's palate. Specifically, the palatal expanders include expansion screws with movable bodies having anatomically contoured palatal surfaces that do not impinge palate tissue during jaw widening procedures. The expansion screws may further include features that allow for reduced hindrances to speech and eating during jaw widening procedures.

BRIEF DESCRIPTION OF THE DRAWINGS

Further details, aspects, and embodiments of the invention will be described by way of example only and with reference to the drawings. In the drawings, like reference numbers are used to identify like or functionally similar elements. Elements in the figures are illustrated for simplicity and clarity and have not necessarily been drawn to scale.

DETAILED DESCRIPTION OF THE INVENTION

In the following description, various embodiments of the present technology will be described. For purposes of explanation, specific configurations and details are set forth in order to provide a thorough understanding of the embodiments. However, it will also be apparent to one skilled in the art that the present technology may be practiced without the specific details. Furthermore, well-known features may be omitted or simplified in order not to obscure the embodiment being described.

As used herein, terms noting anatomical plane views are used to denote geometries of the disclosed embodiments of expansion screws relative to an anatomical plane based on the expansion screws being in an installed configuration in the patient's jaw. For example, the frontal plane corresponds to a plane dividing the patient's body into anterior and posterior portions. A frontal plane is generally considered to be vertical and can show left and right portions of a patient's body and can show top and bottom portions of a patient's body. Further for example, the transverse plane corresponds to a plane dividing the patient's body into top and bottom portions. A transverse plane is generally considered to be horizontal and can show left and right portions of a patient's body and anterior and posterior portions of the patient's body. Further for example, the sagittal plane corresponds to a plane dividing the patient's body into left and right portions. A sagittal plane is generally considered to be vertical and can show top and bottom portions of a patient's body and can show anterior and posterior portions of the patient's body.

As used herein the terms front (anterior), back (posterior), left, right, top (superior) and bottom (inferior) are used to refer to portions of the disclosed expansion screw. The directions correspond to the expansion screw when installed in a patient and correspond to the directional terms of the patients mouth. For example, as used herein a left side of the expansion screw is the side on the left side of the patient's midsagittal plane. The left side of the expansion screw may depicted on the left, right, top or bottom of a figures and depends on the orientation of the figure relative to the patient.

Figure 2:
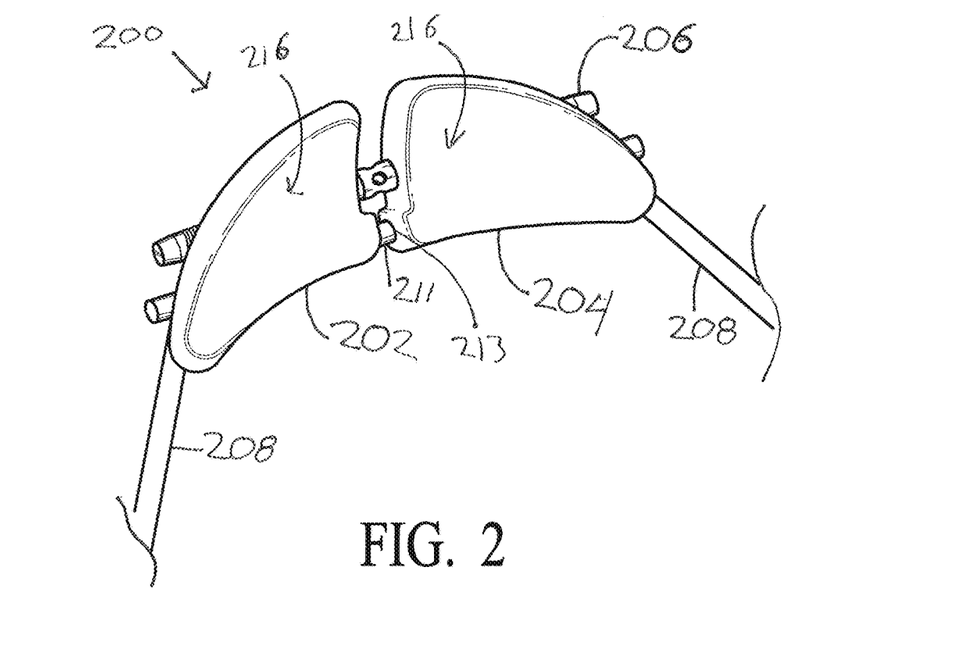
FIGS. 2 and 3 show perspective views of an expansion screw.
Figure 3:
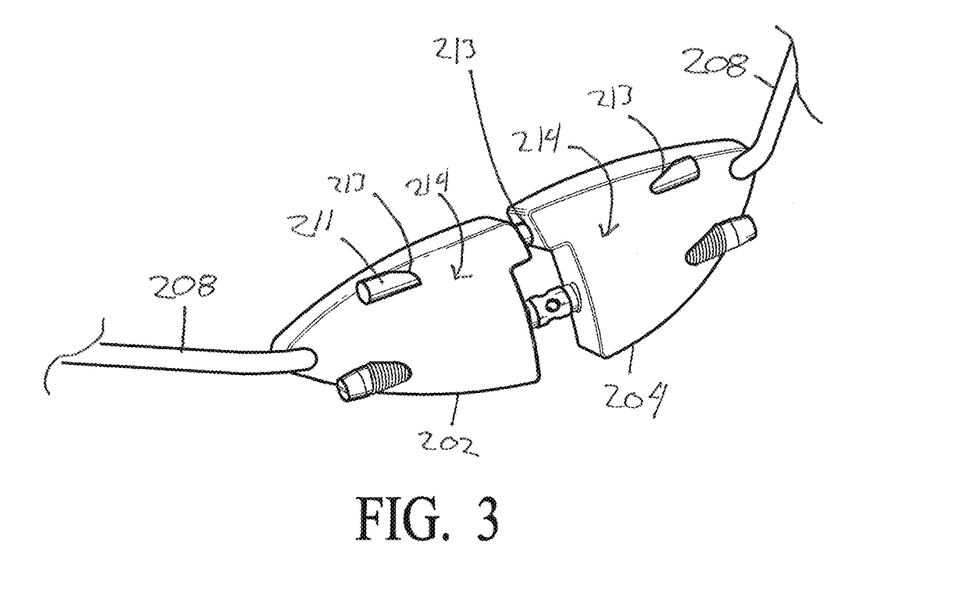

FIGS. 2 and 3 show an embodiment of an orthodontic expansion screw 200. As noted above, expansion screws may be used for widening the upper jaw of a patient. As shown, embodiments of expansion screws 200 include a spindle 206, and two movable bodies comprising a first body 202 and a second body 204 coupled to the spindle 206. Further, in embodiments, expansion screws 200 may further include supporting wires 208 coupled to each of the movable bodies 202 and 204 and molar bands 210 coupled to ends of the supporting wires 208 opposite the moveable bodies 202 and 204. Further, in embodiments, expansion screws 200 may further comprise guide rods 211 slidably coupled to the movable bodies 202 and 204 in order to maintain the relative orientation of the movable bodies in directions normal to the sliding direction. As will be discussed in greater detail below, each of the bodies 202 and 204 include a palatal surface 214 on a top side.

Figure 4:
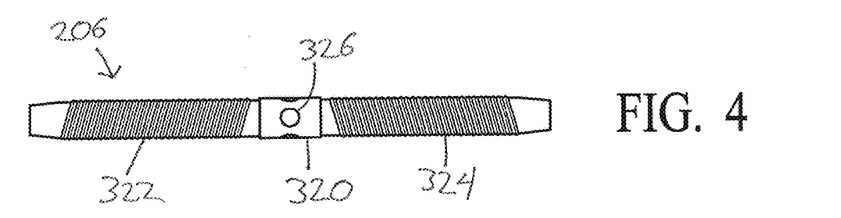
FIG. 4 shows a spindle.

FIG. 4 shows an embodiment of a spindle 206. As shown, in embodiments, a spindle comprises a central actuating portion 320, a left threaded portion 322 and a right threaded portion 324 on opposite sides of the central actuating portion 320. The threaded portions are configured to threadably couple with spindle bores of the movable bodies, and are threaded in opposite directions so that rotation of the spindle causes the coupled bodies to translate relative to each other in opposite directions. In embodiments, the actuating element comprises engagement slots 326 around a circumference of the actuating element configured to receive a tool that the patient or practitioner may insert into the patients mouth to rotate the spindle to cause the bodies to translate relative to each other in order to apply a force to the molars through the supporting wires. In embodiments, the spindle may include a ratchet or other locking mechanism to prevent reverse rotation of the spindle and prevent the bodies from undesirably moving towards each other.

Figure 5A:
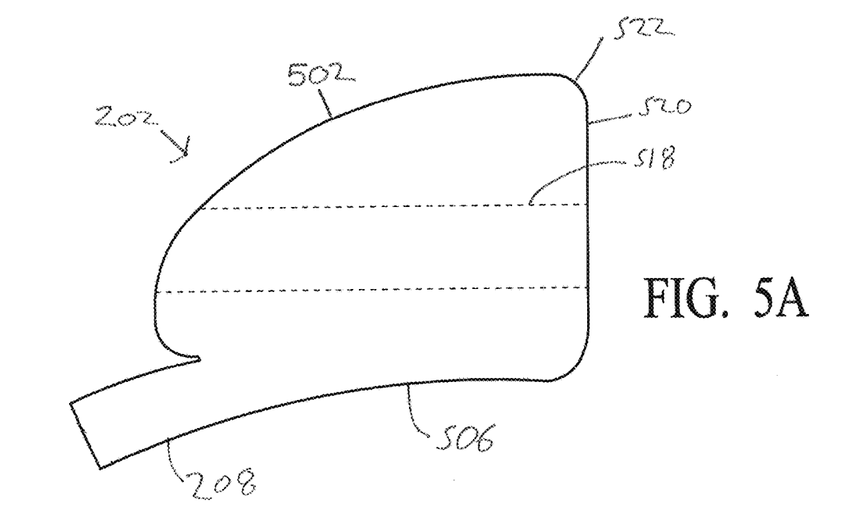
FIG. 5A shows a frontal profile view of a body of an embodiment of an expansion screw.

FIG. 5A shows an embodiment of a first body 202. As shown first body is intended to be installed in a patient on the patient's left side and second body 204 is intended to be installed in a patient on the patient's right side. Geometries of a movable body will be described below in relation to the first body 202, however it is to be understood that the second body 204 may have similar or substantially identical mirror image geometries. In embodiments, the left and right bodies of an expansion screw may be mirror image identical, or may have different features as described herein.

In embodiments, a body may comprise a convex curved profile 502 in a frontal plane view from the anterior side of the body, for example as shown in the profile of first body 202 in FIG. 5A. The convex curved profile 502 of first body 202 comprises the top side and outer left side of the profile in the frontal plane view. The curve of the convex curved profile 502 may have a constant or variable radius of curvature. The radii of curvature are configured to be complementary to the curvature of the frontal plane vertical arch cross-section of the patient's palate at a location adjacent to where the posterior end of the body is intended to be installed in the patient's mouth. Having a complementary shape has the benefit of allowing the bodies to be positioned close to the top of the arc of the palate in order to reduce hindrances to eating and/or speaking. Further, the curvature is beneficial in preventing sharp edges impinging the palate tissue and causing discomfort to the patient when the bodies are translated away from each other during expansion of the jaw.

Figure 5B:
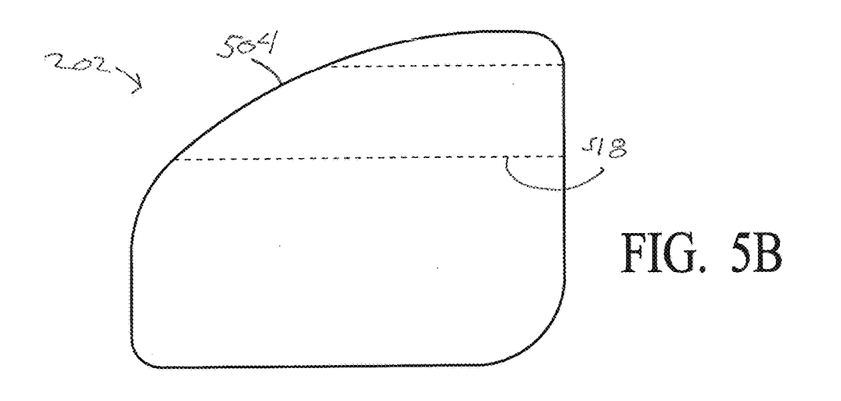
FIG. 5B shows a transverse profile view of a body of an expansion screw.

In embodiments, bodies may include a convex curved profile 504 in a transverse plane view, for example as shown in FIG. 5B. As shown, looking at body 202 from above, the front and left portions of the perimeter of the body have a convex curved profile 504. When installed in a patient's mouth the front and left portions of the body are configured to face in the direction away from the central sagittal plane and in the direction of the teeth. The curve of the convex curved profile 504 may have a constant or variable radius of curvature. The radii of curvature are configured to be complementary to the curvature of the arch in a horizontal cross-section of the patient's palate at a location adjacent to where the body is intended to be installed in the patient's mouth. As shown in FIG. 5B, the convex curved profile 504 leads to the anterior portion of the body being narrower than the posterior portion of the body. This curved profile in the transverse plane view contours to a shape of an anterior end portion the palate of the patient. Having a complementary shape has the benefit of allowing the bodies to be positioned close to the front of the palate in order to reduce hindrances to eating and/or speaking. Further, the curvature is beneficial in preventing sharp edges impinging the palate tissue and causing discomfort to the patient when the bodies are translated away from each other during expansion of the jaw.

In embodiments, bodies may include a convex curved profile in a sagittal plane view. For example the top and front portions of the perimeter of the body in the sagittal plane view have a convex curved profile. This perimeter is configured to face in the direction toward the top (superior) and front (anterior) portions of the palate. The curve of the convex curved profile may have a constant or variable radius of curvature. The radii of curvature are configured to be complementary to the curvature of the arch in the sagittal plane of the patient's palate at a location adjacent to where the body is intended to be installed in the patient's mouth. Having a complementary shape has the benefit of allowing the bodies to be positioned close to the front (anterior) side of the palate of the patient in order to reduce hindrances to eating and/or speaking. Further, the curvature is beneficial in preventing sharp edges impinging the palate tissue and causing discomfort to the patient when the bodies are translated away from each other during expansion of the jaw.

The surfaces of the bodies intended to face the palate of the patient in the installed state of the expansion screw are referred to as the palatal surfaces 214. In embodiments, the palatal surface may be curved, for example substantially cylindrical or substantially spherical. In embodiments, a body may have any combination of one or more of the convex curved profiles described above. The combination of convex curved profiles 502 and 504 may define the surface curvature of the palatal surface 214. For example, a body may have convex curved profiles in the frontal, transverse and sagittal planes that define a substantially spherical curved palatal surface 214, as shown in FIG. 3. The palatal surface may contour to the shape of an anterior end portion the palate of the patient.

In embodiments, for example as shown in FIG. 5A, the inferior side of the bodies may include a concave profile 506 defining a portion of a concave surface 216 configured to face the tongue. The concave inferior side surfaces of the bodies of an expansion screw may form a continuous arch configure to be contoured to the superior curvature of the tongue in order to increase comfort and reduce hindrances to eating and/or speaking.

Figure 8:
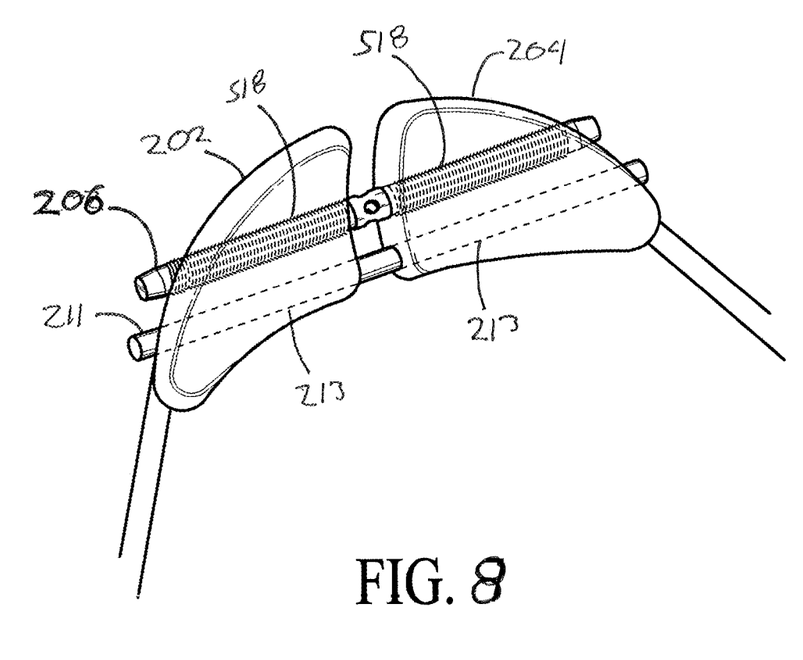
FIG. 8 shows a transparent view of an embodiment of an expansion screw.

In embodiments, the bodies 202 and 204 include a spindle bore extending through the inner side of the body. For example as shown in FIGS. 5A and 8 the spindle bore 518 extends through the inner side 520, which for the left body is the right side of the left body. In embodiments, the spindle bore is generally normal to the sagittal plane so that the longitudinal axis of the spindle bore extends through the inner side and through the palatal surface 214 of the body, so that translation of the bodies due to rotation of the spindle is in a direction normal to the sagittal plane. A shown in FIGS. 5A and 5B, the inner side 520 of a body may be generally flat, which provides the benefit of allowing the bodies to be positioned close together in a first un-spread configuration. In embodiments, the perimeter of the inner surface 520 interfacing with the palatal surface 214 has an atraumatic filleted edge 522 to prevent discomfort if the edge contacts the palate of the patient during use of the device for palate expansion.

Figure 6A:
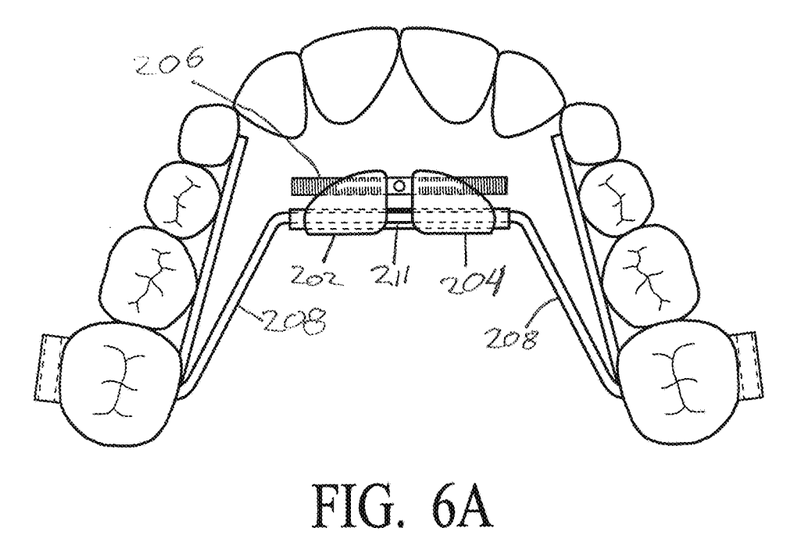
FIG. 6A shows a transverse plane view of an embodiment of an expansion screw in a first un-spread configuration.

The spindle bore 518 includes a threaded interior surface configured to threadably engage and couple to the spindle 206. The threading of opposite bodies of the expansion screw have opposite threading so that rotation of the spindle causes the bodies to translate in opposite directions relative to each other. In embodiments, the spindle bore may be a blind hole and not extend through the palatal surface. A blind hole provides the advantages of a smooth palatal surface and prevents the end of the spindle from contacting and impinging the palate tissues. In embodiments, the spindle bore 518 may extend through the palatal surface 214, for example as shown in FIG. 3. In embodiments wherein the spindle bore extends through the palatal surface, this arrangement allows for the threaded portions of the spindle to extend beyond the convex curved portions in the frontal plane view, as shown in FIG. 6A. Having the spindle extend through the palatal surface provides the advantage of allowing the expansion screw to have a greater amount of horizontal translation which is defined by the length of the engagable threaded portion of the spindle less the minimum amount of engagable threaded portion of the spindle that remains in the threading of the spindle bore in a fully spread configuration. In embodiments, the lengths of the threaded portions of the spindle and spindle bore are configured to translate the bodies greater than 12 mm, for example 14 mm, 16 mm, or 18 mm. In embodiments, the spindle may be interchangeable with spindles of different lengths to obtain the desired amount of translation distance for a jaw widening application.

Figure 6B:
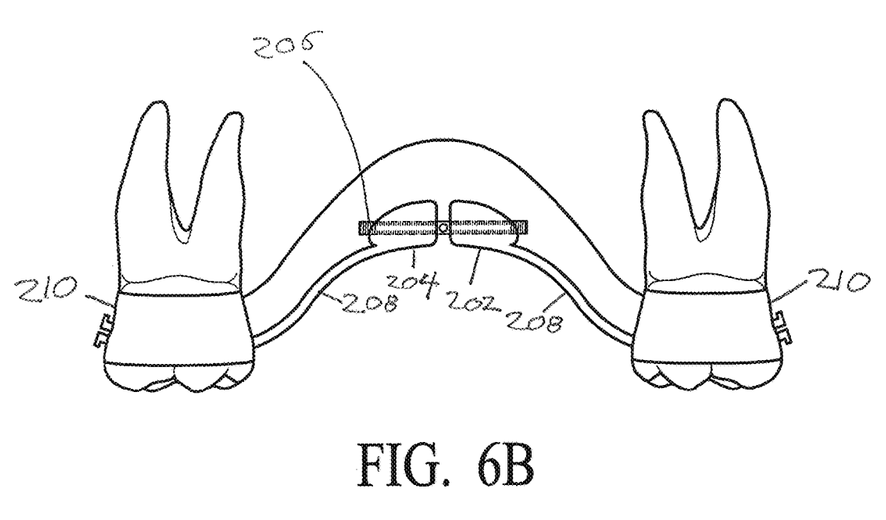
FIG. 6B shows a frontal plane view of an embodiment of an expansion screw in a in the first un-spread configuration.
Figure 6C:
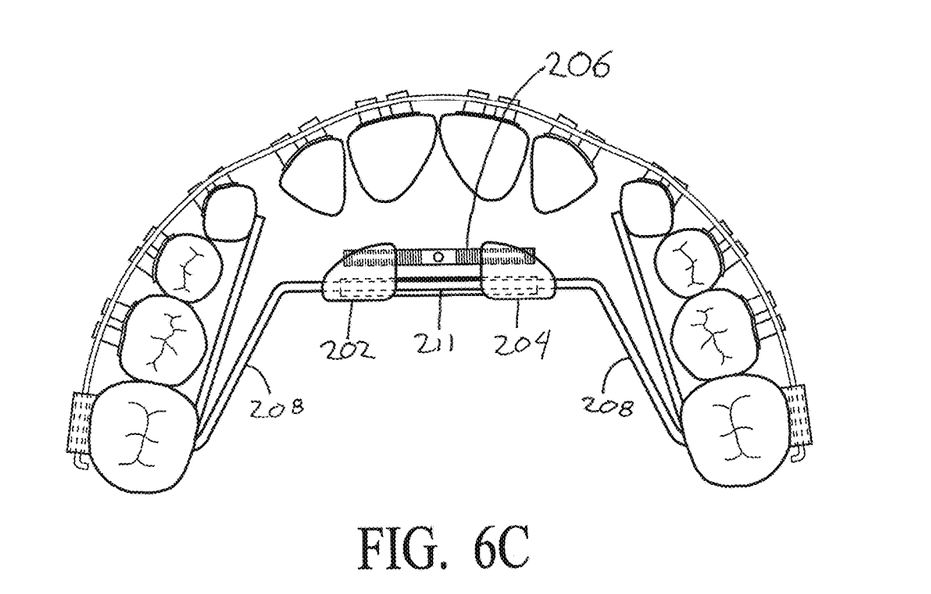
FIG. 6C shows a transverse plane view an embodiment of an expansion screw in a second spread configuration.
Figure 6D:
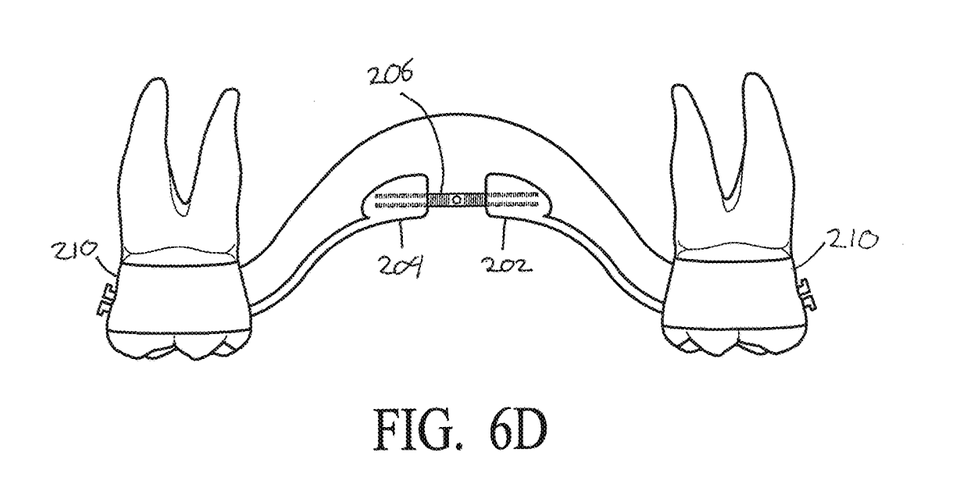
FIG. 6D shows a frontal plane view of an embodiment of an expansion screw in the second spread configuration.

As noted above, the expansion screw 200 may further comprise supporting wires 208, for example as shown in FIG. 2. The supporting wires 208 may be coupled to the inferior side of the bodies 202 and 204 for example as shown in FIGS. 5A and 6B, or may be coupled to the palatal surface for example as shown in FIGS. 2 and 3. As noted above, the supporting wires 208 are coupled to molar bands 210 and configured to exert a horizontal force between the left and right molar bands in response to translation of the left and right bodies from an unspread configuration, as shown in FIGS. 6A and 6B, to a spread configuration, as shown in FIGS. 6C and 6D. In embodiments, for example as shown in FIGS. 6B and 6D, the supporting wire 208 coupled to the first body 202, the inferior side of the first body 202, the inferior side of the second body 204, and the supporting wire coupled to the second bod 204 form a smooth concave inferior side profile in the frontal plane view in both the spread and un-spread configurations, and configuration in between. The smooth concave inferior side profile is free from sharp transitions so as to accommodate a tongue of the patient without causing discomfort or hindering speech or eating. While the figures show only one supporting wire coupled to each body, in embodiments more than one supporting wire may be coupled to each body and one or more supporting wire may be coupled to one or more molar bands or premolar bands.

In embodiment, expansion screws 200 may further include guide rods 211 slidably coupled to guide bores 213 in the bodies 202 and 204, for example as shown in FIG. 8. Guide rods 211 allow the bodies to translate along a straight line in a plane, perpendicular to the suture and prevents relative rotation of the bodies to one another. The guide rods and guide bores extend parallel to the spindle and spindle bore. In embodiments, the longitudinal axis of the guide rod and the longitudinal axis of the spindle may be on the same transverse plane in order for the expansion screw to be more compact in the vertical direction and closer to the patient's palate in order increase vertical tongue space and reduce hindrance of speech and eating. In embodiments the guide bores are blind holes, or in embodiments the guide bores extend through the palatal surface 214, for example as shown in FIG. 3, and allow for greater travel of the bodies while also providing the advantage of prevention of relative rotation of the bodies.

In embodiments, to use expansion screws as disclosed herein a model, for example a plaster mold, of the patient's upper jaw is made. An expansion screw is selected based on complementary curvature of the palatal surfaces of the bodies. The expansion screw may be selected from a plurality of expansion screws with bodies having different curvatures of the palatal surfaces. The selected expansion screw may then be positioned in the model so that the central actuating portion of the spindle will be accessible by the patient with a tool when installed in the patients mouth. The expansion screw may be further positioned to avoid interference with the patient's tongue and palate tissue. In embodiments, supporting wires may then be coupled to the molar bands, for example by soldering, or otherwise adhering, to the molar bands so that the expansion screw when installed on the patient's molars will be positioned at the selected position. The expansion screw may then be cemented in the patient's mouth with the molar bands. In embodiments, the expansion screw may further be positioned within the patient's mouth via anchors coupled to the guide rod between the bodies and extending into the patient's palate tissue.

Once installed, the patient may be given instructions to turn the spindle, via a tool inserted into the engagement slots in the actuating portion, once a day. This turning causes the bodies to translate in a horizontal plane from an un-spread configuration as shown in FIGS. 6A and 6B, to a spread configuration as shown in FIGS. 6C and 6D. As shown in FIGS. 6C and 6D, in the spread configuration no corners of the bodies 202 and 204 impinge into the palate tissue 114. Further, the supporting wires 208 coupled to inferior sides of the bodies 202 and 204 do not impinge into the palate tissue 114.

Figure 7A:
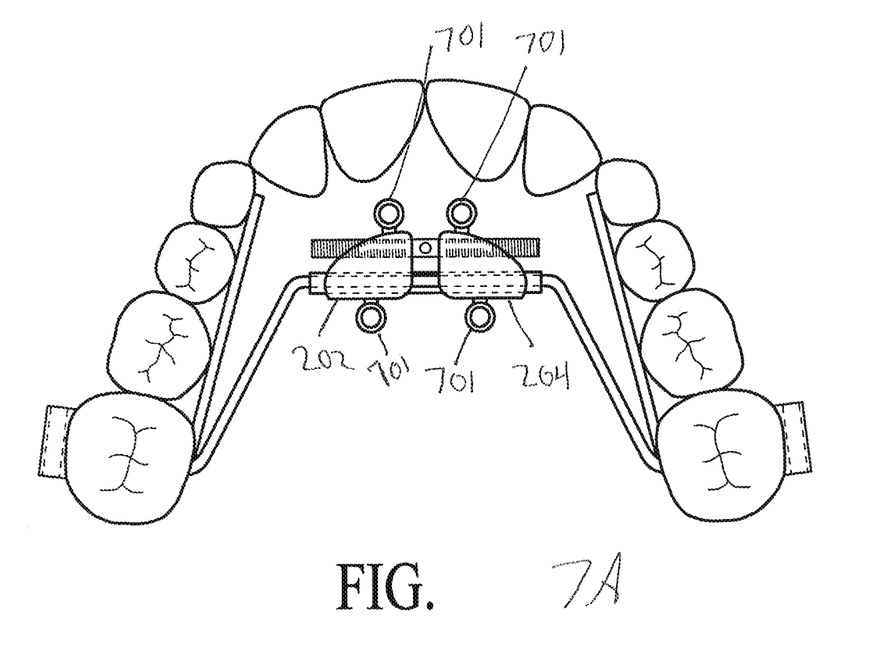
FIGS. 7A and 7B show an embodiment of an expansion screw including bone anchors.
Figure 7B:
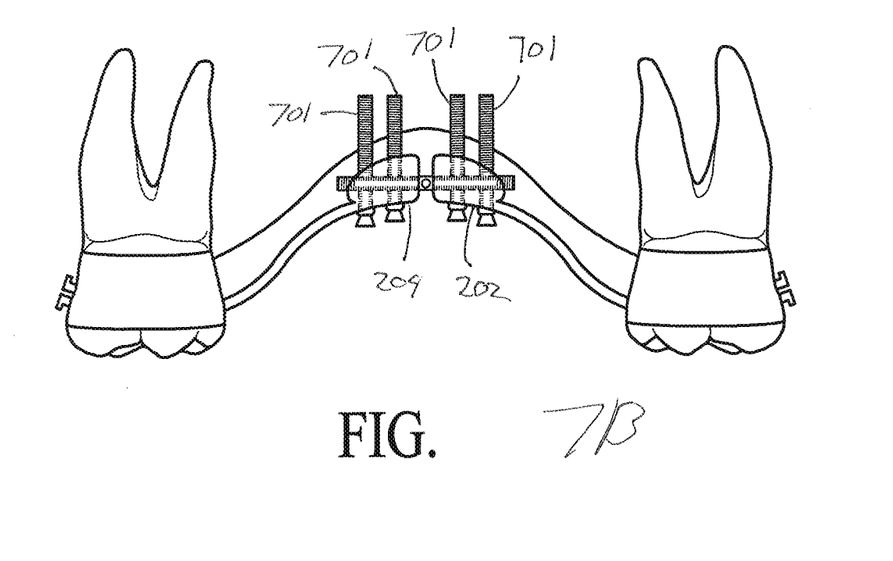

In embodiments, bodies may include bone anchors 701 threadably coupled to anterior and posterior sides of the bodies, for example as shown in FIGS. 7A and 7B. The bone anchors 701 may include threaded cylinders for anchoring into the palatal bone on either side of the midpalatal suture. Anchoring into the bone provides the advantage of being able to exert more force on the midpalatal suture through the bodies, which is particularly advantageous for older patients whose suture has fused and require more force to break open.

From the foregoing, it will be appreciated that specific embodiments of the invention have been described herein for purposes of illustration, but that various modifications may be made without deviating from the spirit and scope of the various embodiments of the invention. Further, while various advantages associated with certain embodiments of the invention have been described above in the context of those embodiments, other embodiments may also exhibit such advantages, and not all embodiments need necessarily exhibit such advantages to fall within the scope of the invention. Accordingly, the invention is not limited, except as by the appended claims.

References throughout the foregoing description to features, advantages, or similar language do not imply that all of the features and advantages that may be realized with the present technology should be or are in any single embodiment of the invention. Rather, language referring to the features and advantages is understood to mean that a specific feature, advantage, or characteristic described in connection with an embodiment is included in at least one embodiment of the present technology. Thus, discussion of the features and advantages, and similar language, throughout this specification may, but do not necessarily, refer to the same embodiment.

Furthermore, the described features, advantages, and characteristics of the present technology may be combined in any suitable manner in one or more embodiments. One skilled in the relevant art will recognize that the present technology can be practiced without one or more of the specific features or advantages of a particular embodiment. In other instances, additional features and advantages may be recognized in certain embodiments that may not be present in all embodiments of the present technology.

Although certain aspects of the invention are presented below in certain claim forms, the applicant contemplates the various aspects of the invention in any number of claim forms. Accordingly, the applicant reserves the right to pursue additional claims after filing this application to pursue such additional claim forms, in either this application or in a continuing application

What is claimed:
1. An orthodontic expansion apparatus for widening the maxilla of a patient, the apparatus comprising:
  a spindle comprising a central actuating portion, a left threaded portion and a right threaded portion on opposite sides of the central actuating portion;
  a left body threadably coupled to the left threaded portion; and
  a right body threadably coupled to the right threaded portion;
  wherein rotating the central actuating portion causes the left body and the right body to translate in opposite directions along a longitudinal axis of the spindle between an unspread configuration with the left body and the right body proximate to the central actuating portion and a spread configuration with the left body and the right body distal to the central actuating portion, and
  wherein each of the left body and right body comprise a convex curved profile in a frontal plane view configured to face a palate of the patient and to contour to a shape of a superior side of the palate,
  wherein each of the left body and the right body comprise a convex curved profile in a transverse plane view configured to contour to a shape of an anterior end portion of the palate,
  wherein each of the left body and the right body comprise a palatal surface configured to face the palate of the patient,
  wherein the palatal surface is a substantially spherical convex surface defined by the curved profile in the transverse plane view and the curved profile in the frontal plane view, and
  wherein the spherical convex surface is configured to face the palate of the patient and to contour to a shape of the anterior end portion of the palate.

2. The orthodontic expansion apparatus of claim 1, wherein in the unspread configuration, the left threaded portion extends through the left body and beyond the curved profile of the left body, and the right threaded portion extends through the right body and beyond the curved profile of the right body.

3. The orthodontic expansion apparatus of claim 1, wherein in the unspread configuration the left threaded portion extends through the spherical convex surface of the left body, and the right threaded portion extends through the spherical convex surface of the right body.

4. The orthodontic expansion apparatus of claim 1, further comprising:
  a left molar band;
  a right molar band;
  a left support arm extending from the left body and coupled to the left molar band; and
  a right support arm extending from the right body and coupled to the right molar band,
  wherein the left and right supports arms are configured to exert a horizontal force between the left and right molar bands in response to translation of the left and right bodies from the unspread configuration to the spread configuration, and
  wherein the left support arm, left body, right body, and right support arm form a smooth concave bottom profile in the frontal plane view without sharp transitions between the left support arm and the left body or the right support arm and the right body so as to accommodate a tongue of the patient.

5. The orthodontic expansion apparatus of claim 1, further comprising a guide rod slidably coupled to the right body and the left body, wherein the longitudinal axis of the spindle and a longitudinal axis of the guide rod are on a plane substantially parallel to a transverse plane of the patient.

6. The orthodontic expansion apparatus of claim 1, wherein translation between the right body and the left body between the unspread configuration and the spread configuration comprises greater than 12 mm of travel without the risk of causing palatal impingement.

7. The orthodontic expansion apparatus of claim 1, further comprising a first bone anchor coupled to the left body, and a second bone anchor coupled to the right body, wherein the first and second bone anchors are configured to anchor into a palate bone of the palate.

\* \* \* \* \*